United States Patent
Haris et al.

(10) Patent No.: US 10,791,989 B2
(45) Date of Patent: Oct. 6, 2020

(54) MAGNETIC RESONANCE IMAGING OF POLY-L-GLUTAMATE

(71) Applicant: The Trustees of The University of Pennsylvania, Philadelphia, PA (US)

(72) Inventors: Mohammad Haris, Philadelphia, PA (US); Anup Singh, Philadelphia, PA (US); Kejia Cai, Elkins Park, PA (US); Ravinder Reddy, Gladwyne, PA (US); Feliks Kogan, Philadelphia, PA (US); Ravi Prakash Reddy Nanga, Philadelphia, PA (US); Hari Hariharan, Mount Laurel, NJ (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 941 days.

(21) Appl. No.: 14/781,441

(22) PCT Filed: Apr. 4, 2014

(86) PCT No.: PCT/US2014/033003
§ 371 (c)(1),
(2) Date: Sep. 30, 2015

(87) PCT Pub. No.: WO2014/165775
PCT Pub. Date: Oct. 9, 2014

(65) Prior Publication Data
US 2016/0041245 A1    Feb. 11, 2016

Related U.S. Application Data

(60) Provisional application No. 61/809,193, filed on Apr. 5, 2013.

(51) Int. Cl.
*A61B 5/055*    (2006.01)
*A61B 5/00*    (2006.01)
(Continued)

(52) U.S. Cl.
CPC ............ *A61B 5/4848* (2013.01); *A61B 5/055* (2013.01); *A61B 5/14546* (2013.01);
(Continued)

(58) Field of Classification Search
CPC ............ G01R 33/5601; G01R 33/5605; G01R 33/4828; A61B 5/055; A61B 6/481; C12Q 1/6886
See application file for complete search history.

(56) References Cited

U.S. PATENT DOCUMENTS

| 4,678,995 A | 7/1987 | Avison et al. |
| 2002/0101238 A1 | 8/2002 | Watanabe |

(Continued)

OTHER PUBLICATIONS

Balchandani, et al., "Fat Suppression for 'H MRSI at 7T Using Spectrally-Selective Adiabatic Inversion Recovery," Magn Reson Med., May 2008, 59(5), 980-988.
(Continued)

*Primary Examiner* — Elmer M Chao
(74) *Attorney, Agent, or Firm* — BakerHostetler (57) ABSTRACT

A non-invasive imaging approach using CEST and MRS may be used to monitor the cleavage of the poly-L-glutamate (PLG) backbone. The cleavage of PLG by cathespsin B can expose exchangeable —NH2 protons in the PLG that are then monitored non-invasively through CEST. The technique can provide direct information on malignant tissue and tumor aggressiveness, and can also be used to monitor treatment.

17 Claims, 5 Drawing Sheets

(51) Int. Cl.
  *G01R 33/56*  (2006.01)
  *A61M 5/00*  (2006.01)
  *A61B 5/145*  (2006.01)
  *G01R 33/46*  (2006.01)
  *G01R 33/483*  (2006.01)

(52) U.S. Cl.
  CPC .......... *A61B 5/4064* (2013.01); *A61B 5/4839* (2013.01); *A61B 5/4866* (2013.01); *A61M 5/007* (2013.01); *G01R 33/46* (2013.01); *G01R 33/483* (2013.01); *G01R 33/5601* (2013.01); *G01R 33/5605* (2013.01); *A61B 2560/0475* (2013.01); *A61B 2576/00* (2013.01)

(56) References Cited

U.S. PATENT DOCUMENTS

| | | | |
|---|---|---|---|
| 2007/0134159 A1 | 6/2007 | Dixon et al. | |
| 2009/0176218 A1 | 7/2009 | Cheng et al. | |
| 2010/0290997 A1 | 11/2010 | Li et al. | |
| 2012/0019245 A1 | 1/2012 | Reddy et al. | |
| 2012/0108944 A1 | 5/2012 | Turek et al. | |
| 2013/0195768 A1* | 8/2013 | Aime | A61K 49/106 424/9.363 |
| 2014/0087362 A1* | 3/2014 | Szalay | C07K 14/00 435/5 |

OTHER PUBLICATIONS

Cai, et al. "Breast Cancer Redox Heterogeneity Detectable with Chemical Exchange Saturation Transfer (CEST) MRI," Mol. Imaging Bioi., May 9, 2014, 10 pgs.

Cantor, et al. "Cancer Cell Metabolism: One Hallmark, Many faces," Cancer Discov, Sep. 25, 2012, vol. 2(10), 881-898.

Li, et al. "Imaging Mitochondrial Redox Potential and its Possible Link to Tumor Metastatic Potential," J Bioenerg Biomembr, Dec. 1, 2012, vol. 44, pp. 645-653.

Penner, et al. "Metabolite Nulling to measure the Macromolecule Baseline for Quantitative $^1$H Magnetic Resonance Spectroscopy at 7 Tesla," Proc. Inti. Soc. Mag. Reson. Med., 2010, p. 911.

Periasamy, et al "Tea polyphenols Modulate Antioxidant Redox System on Cisplatin-Induced Reactive Oxygen Species Generation in a Human Breast Cancer Cell." Basic Clin Pharmacal Toxicol, Jan. 24, 2013, vol. 112, 374-384.

Ratnakar, et al. "Europium(III) DOTA-tetraamide Complexes as Redox-Active MRI Sensors," J. Am Chem. Soc, Mar. 23, 2012, vol. 134, 5798-5800.

Schafer et al. "Redox Environment of the Cell as Viewed Through the Redox State of the Glutathione Disulfide/Glutathione Couple," Free Radic Bioi Med, Jun. 1, 2001, vol. 30, 1191-1212.

Rothman et al., "Localized 1H NMR measurements of γ-aminobutyric acid in human brain in vivo", Proc. Natl. Acad. Sci, USA, Jun. 1993, Neurobiology, vol. 90, pp. 5662-5666.

* cited by examiner

MAGNETIC RESONANCE IMAGING OF POLY-L-GLUTAMATE

CROSS-REFERENCE TO RELATED APPLICATIONS

This application is a National Stage Application filed under 35 U.S.C. 371 of International Application No. PCT/US2014/033003, filed Apr. 4, 2014, which claims the benefit of priority of U.S. Provisional Patent Application No. 61/809,193, filed Apr. 5, 2013, titled Magnetic Resonance Imaging of Poly-L-Glutamate, the contents of which is hereby incorporated by reference herein in its entirety, for all purposes.

GOVERNMENT RIGHTS

This invention was made with government support under grant number EB015893 awarded by the National Institutes of Health. The government has certain rights in the invention.

TECHNICAL FIELD

The technical field generally relates to magnetic resonance and more specifically relates to chemical exchange saturation transfer imaging techniques.

BACKGROUND

Chemical Exchange Saturation Transfer (CEST) is a technique that provides an indirect way of detecting the signal from exchangeable protons with bulk water in magnetic resonance imaging (MRI). CEST imaging uses an off-resonance saturation pulse at the resonance frequency of exchanging protons to null the signal from exchangeable protons in order to indirectly decrease bulk water signal through chemical exchange, creating a detectable contrast from bulk waters.

Invasion and metastasis of tumor cells require the action of tumor-associated proteases. Proteolytic enzymes such as cathepsins B, D, and L are involved in the degradation of components of the extracellular matrix and the basement membranes. The quantitative expression of cathepsins enzyme family has been widely used to demonstrate the malignancy in cancer. Significantly higher expression of cathepsin B and cathepsin L has been observed in malignant and benign or less aggressive tumors. However, quantification of cathepsins enzymes by biochemical methods is invasive and requires tissue excision and prolonged immunhistochemical analysis.

Poly(L-glutamic acid) (PLG) has been used as a macromolecular carrier for drug delivery, specifically to target cancer. The PLG is a polymer of L-glutamic acid and is non-toxic. The polymer conjugated drug, PLG-paclitaxel (PG-TXL, CT2103, Xyotax) has advanced to phase III clinical trials, and PLG-camptothecin (CT2106) has been tested in phase II clinical trials. The selective proteolysis of the PLG backbone through the action of cellular proteases in cancer tissues is responsible for the increased site-specific delivery and enhanced antitumor activity of PLG-bound TXL. Cysteine proteases, particularly cathepsin B, play a key role in the lysosomal degradation of PLG.

Detection of enzymatic cleavage of PLG backbone has been performed in vivo using fluorescence optical imaging. However, imaging using optical probes in vivo in human patients has limited utility due to the need for the presence of a dye moiety. It is desired to image the PLG backbone using MR imaging techniques that do not require dyes.

SUMMARY

A non-invasive imaging approach using CEST and magnetice resonance spectroscopy (MRS) may be used to monitor the cleavage of the Poly-L-glutamate (PLG) backbone. In an embodiment, the cleavage of PLG by cathespsin B can expose exchangeable —NH2 protons in the PLG that are then monitored non-invasively through CEST. The technique can provide direct information on malignant tissue and tumor aggressiveness, and can also be used to monitor treatment.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to limitations that solve any or all disadvantages noted in any part of this disclosure.

BRIEF DESCRIPTION OF THE DRAWINGS

A more detailed understanding may be had from the following description, given by way of example in conjunction with the accompanying drawings wherein.

DETAILED DESCRIPTION OF ILLUSTRATIVE EMBODIMENTS

Magnetic resonance imaging (MRI) provides a way to detect the tissue contrast in vivo non-invasively and proton MR spectroscopy (MRS) provides metabolite information. Imaging of small metabolites in vivo at high resolution can be performed using a technique commonly known as chemical exchange saturation transfer (CEST) MRI. The CEST contrast arises from exchangeable protons (—NH, —NH$_2$, and —OH) of different metabolites. As explained herein, high-resolution imaging of glutamate can be performed by exploiting its labile —NH$_2$ protons using a CEST method. In particular, disclosed herein is the cleavage of PLG by protease (e.g., cathepsin B) into smaller residues that expose exchangeable —NH$_2$ protons in PLG which can be monitored non-invasively through CEST. The cleavage of PLG in vivo can be monitored using proton MRS at lower resolutions. Though using both CEST and MRS it is possible to monitor the PLG cleavage, CEST MRI method provides higher resolution image of enzymatic cleavage of PLG and therefore enzyme expression. Moreover, heterogeneity of enzyme expression can be monitored specifically through CEST MRI method. Generally, CEST can be defined as an MRI method to image metabolites or macromolecules possess labile protons which exchange with water protons, while MRS provides information about the metabolites based on their aliphatic protons.

Higher expression of cathepsin and other proteases (for example, cathepsin B) in a malignant tumor results in more cleavage of PLG backbone. Benign tumors express less protease enzymes than a malignant tumor and thus the amount of PLG cleavage in these tumors will be different, which can be monitored. The aggressiveness of tumor tissue is associated with the higher expression of the protease enzyme. The aggressiveness of tumor can be measured by mapping the amount of PLG cleavage by protease enzymes expressed in tumor tissue. By using CEST and MRS, the degree of PLG backbone cleavage can be monitored non-invasively. This can be used as a biomarker to observe the enzyme activity/expression in vivo, to monitor progression of a tumor, and to predict tumor malignancy. Such methods and processes can be used in diagnosis and treatment monitoring of various cancers including breast, prostate, ovarian, and brain, among others.

The same techniques and approaches described here can also be used for assessing the fate of polymer conjugated chemotherapeutic drugs in preclinical as well as in clinical studies. PLG has been used as a macromolecular carrier for drug delivery. Monitoring the cleavage of PLG in PLG conjugated drugs by protease enzyme at the site of tumor can provide information about drug delivery. In the clinical setting, by looking the amount of PLG cleavage through CEST MRI and MRS in a tumor patient, aggressiveness as well as tumor type can be diagnosed. Similarly the therapeutic effect of targeted drugs conjugated with PLG can also be monitored. Killing of tumor cells by anti-cancerous drugs will reduce the protease enzymes expression. By looking at the cleavage of PLG following the drug treatment, efficacy of a particular drug can be monitored.

Phantoms with glutamate, PLG, and PLG+cathepsin B were prepared and experiments were performed at room temperature on a 7T whole-body scanner. Both the CEST imaging and MRS were performed. To further prove the concept, an additional experiment was performed at 9.4 T animal scanner on F98 tumor cells line with and without addition of PLG.

Figure 1:
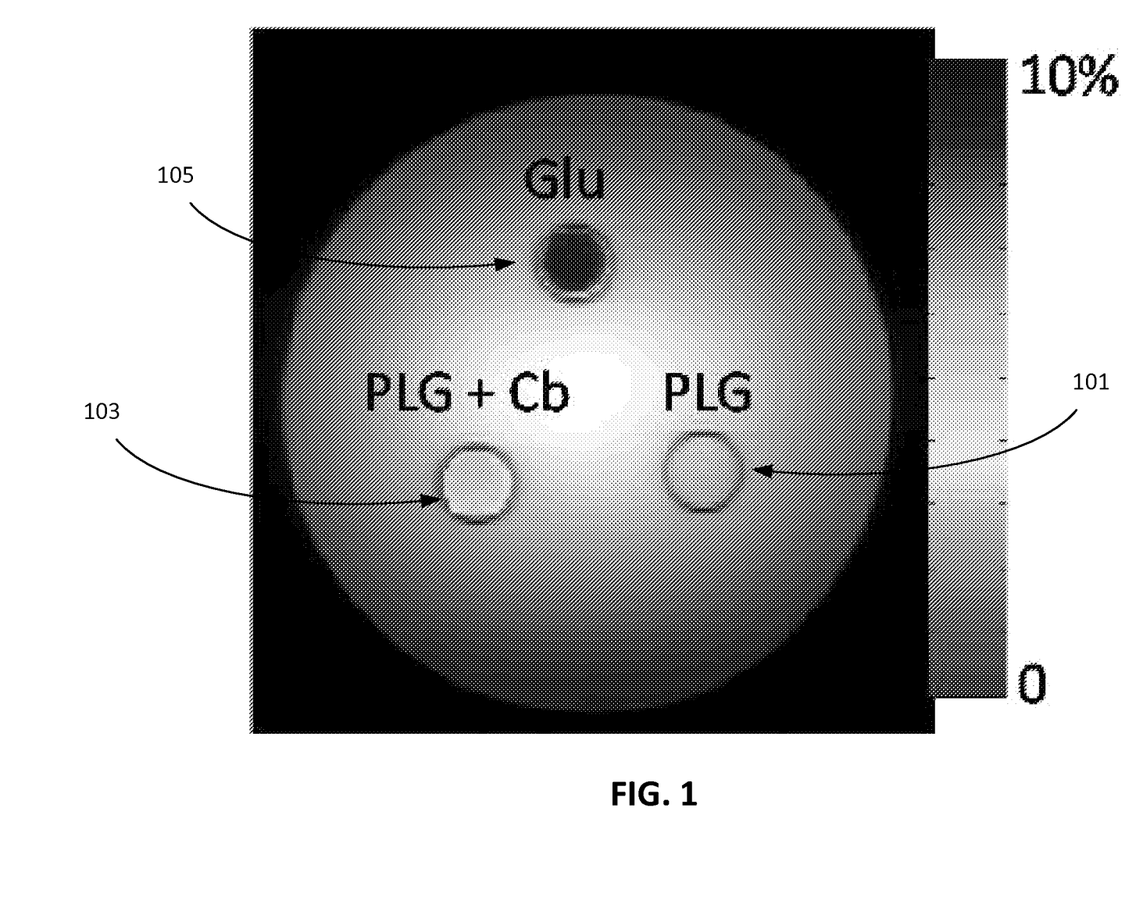
FIG. 1 displays a CEST contrast map of a phantom.

FIG. 1 shows a CEST contrast map at 3 parts per million (ppm) from glutamate at 105, PLG at 101, and PLG with cathepsin B at 103. Glu at 105 shows a strong CEST contrast. No CEST contrast was observed from PLG alone at 101. However, after addition of cathepsin B an appreciable CEST contrast was observed at 103; this is due to the cleavage of PLG into smaller fragments by cathepsin B. This cleavage exposed a significant number of labile —NH$_2$ protons that can be noticeably detected using CEST MRI.

Figure 2:
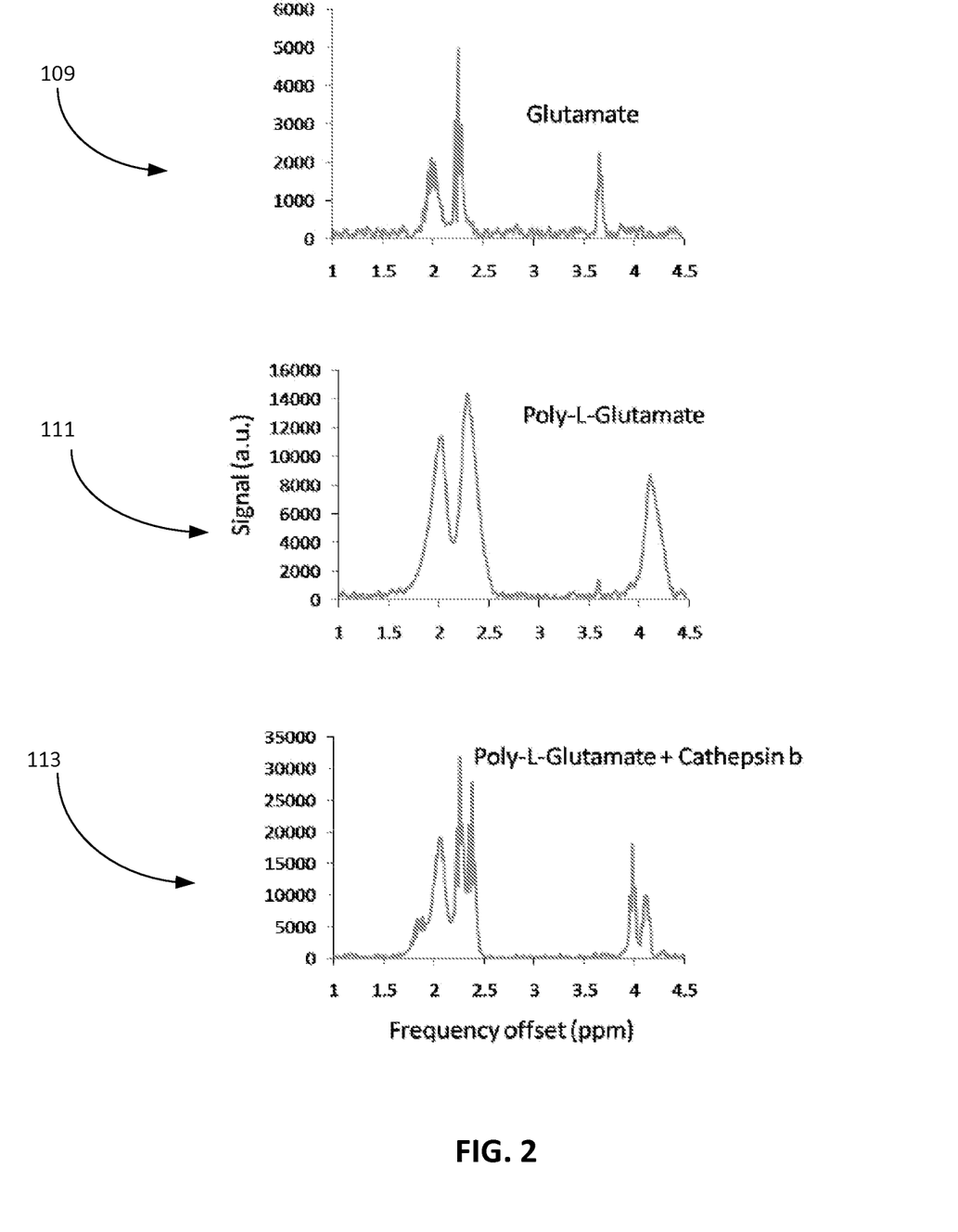
FIG. 2 displays graphs of magnetic resonance spectra from phantoms.

FIG. 2 shows MR spectra from phantoms containing glutamate (graph 109), poly-L-glutamate (PLG) (graph 111), and PLG+cathepsin B (graph 113). Spectrum from glutamate in graph 109 shows multiple peaks at approximately 2, 2.3, and 2.75 ppm. Spectrum from PLG in graph 111 shows three peaks respectively at approximately 2, 2.3, and 4.1 ppm. Phantom with PLG and cathepsin B in graph 113 shows cleavage of 2.3 and 4.1 ppm peaks, which is due to cleavage of PLG by cathepsin B. The extra peak observed in case of PLG+cathepsin B can be used to detect enzyme activity in vivo.

Figure 3:
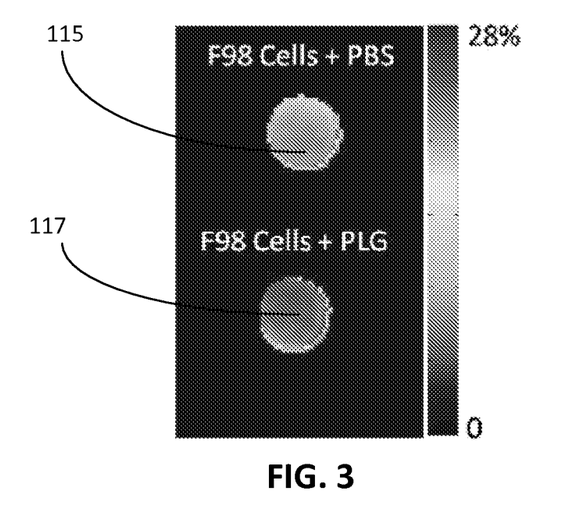
FIG. 3 displays CEST maps from F98 tumor cells.

FIG. 3 illustrates a CEST maps of F98 tumor cells line with PLG incubation at 117 and without PLG incubation at 115. F98 cell line is known to be aggressive and expresses cathepsin B and other proteases. After addition of PLG, a significant (~16%) increase in CEST contrast at 3 ppm is observed which is due to the cleavage of PLG by enzymes. This cleavage exposed more labile —NH$_2$ protons. Thus, expression of enzyme activity in a tumor can be monitored at high resolution using CEST imaging and also the same can be used as a biomarker of imaging tumor aggressiveness and heterogeneity of the tumor.

An in vivo experiment was performed on rats bearing brain tumor (n=3) at 9.4 T animal scanner. Proton spectroscopy and CEST imaging was performed before and after intravenous injection of PLG through tail vein.

Figure 4:
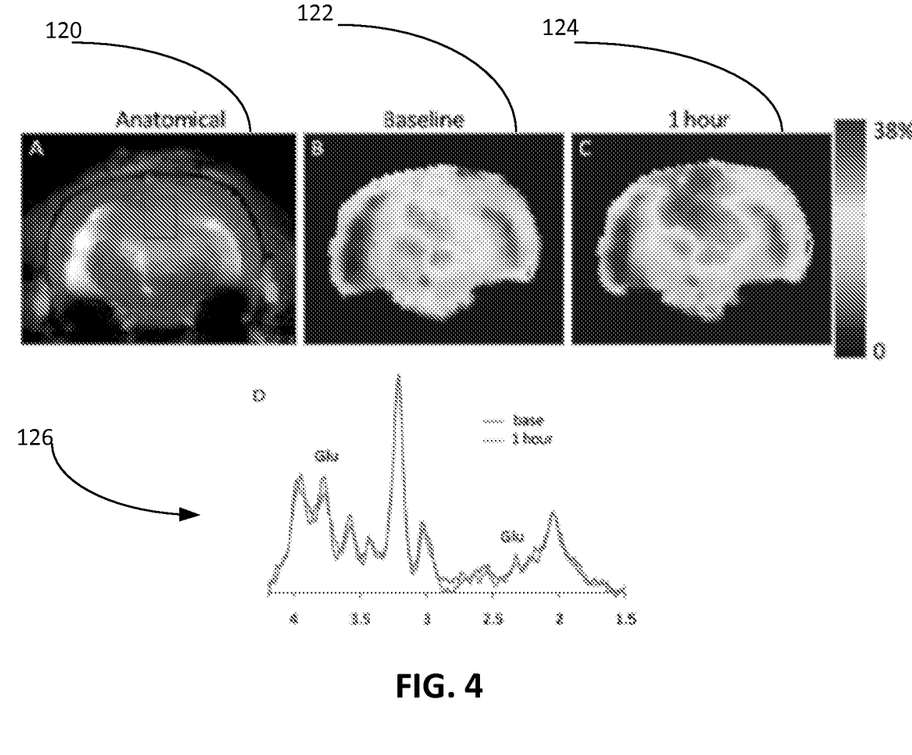
FIG. 4 displays comparisons of CEST maps.

FIG. 4 illustrates a baseline anatomical at 120 and a baseline CEST map at 122 of a rat brain tumor model. From the voxel as shown in 120 of FIG. 4., ~32% increase in CEST contrast at 3 ppm, as shown in 124 in FIG. 4, was observed with concomitant increase in glutamate (~30%) on $^1$HMRS as shown in 126 of FIG. 4, at 1-hour post intravenous injection of PLG (16 mg/kg). It is believed that in in vivo cathepsin enzyme cleaves PLG more rapidly into its monomer, i.e., glutamate, than that of phantom. Due to the continuous synthesis of cathepsin B in tumor while in phantom, a small given amount of cathepsin B enzyme is added, which can probably cleave part of PLG into its oligomer and expose less labile —NH$_2$ protons.

The activity of protease enzymes, such a cathepsin B can be monitored non-invasively using current methods and systems disclosed herein. In vivo monitoring of PLG and related polymer conjugated drug delivery to tumor can be performed non-invasively without injection of any fluorescence conjugated compound. This can be implemented on clinical MRI scanner for routine clinical examination of tumor biology as well as to monitor the therapeutic response, which can help in staging tumor aggressiveness.

The methods and systems discussed herein may be used in the area of targeted drug delivery, such as monitoring the therapeutic responses in animal model of tumor, which may aid in drug discovery. For example, the disclosed methods and systems can be used to monitor anti-tumor drugs, which use PLG as a carrier (e.g., paclitaxel and camptothecin), delivery at site of tumor.

Optical imaging methods have been used to monitor the hydrolysis of PLG by protease enzyme in mouse model of tumor but it requires conjugation of PLG with near infrared fluorescence dye. There is no CEST method that exploits —NH$_2$ group of poly glutamate for imaging the proteases activity in tumor. The same CEST imaging parameters to image PLG cleavage by protease enzyme as well as to image glutamate metabolite may be used. However, the imaging parameters to image the PLG cleavage by protease enzymes can be further optimized to enhance the CEST contrast.

Prior techniques based on optical imaging require injection of PLG conjugated with fluorescence dye and this may lessen its application in human subjects. However, as disclosed herein, only injection of PLG is required which is nontoxic. Disclosed methods and systems allow for mapping of enzyme activity, as well as monitoring of drug delivery response in tumor, which can provide a new image contrast to monitor the tumor aggressiveness in vivo.

The techniques disclosed herein may be used in at least any of the following ways: 1) PLG can be used as a standalone MRI contrast agent and protease enzyme activity in tumor tissue at high resolution; 2) the aggressiveness of tumors can be estimated; 3) the CEST and MRS of PLG can be used for discriminating between benign versus malignant tumors; 4) specific delivery of drugs using PLG as a carrier can be monitored; 5) use in drug discovery/therapy monitoring in animal model studies of different cancers; or 6)

CEST and MRS of PLG can be routinely used in clinical diagnosis of tumor, assess the targeted drug delivery, and also to monitor the therapeutic efficacy.

Figure 5:
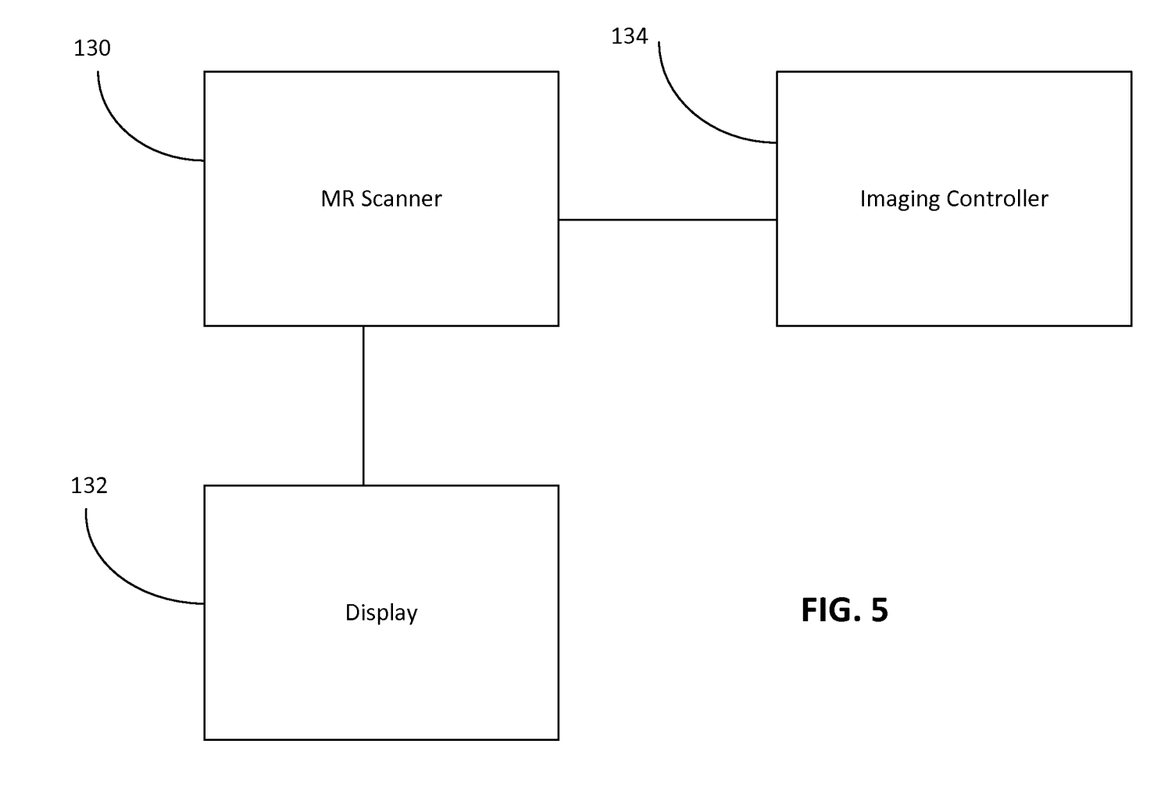
FIG. 5 illustrates a conventional MR scanner that displays the obtained MR images on a display under control of an imaging controller programmed to implement any or all of the CEST imaging pulse sequences and CEST imaging protocols described herein.

FIG. 5 illustrates in rudimentary form a conventional MR scanner 130 that displays the obtained MR images on a display 132. Imaging controller 134 includes a processor programmed to implement any or all of the CEST imaging pulse sequences and CEST imaging protocols described herein. Accordingly, any such modifications are intended to be included within the scope of this invention as defined by the following exemplary claims.

Figure 6:
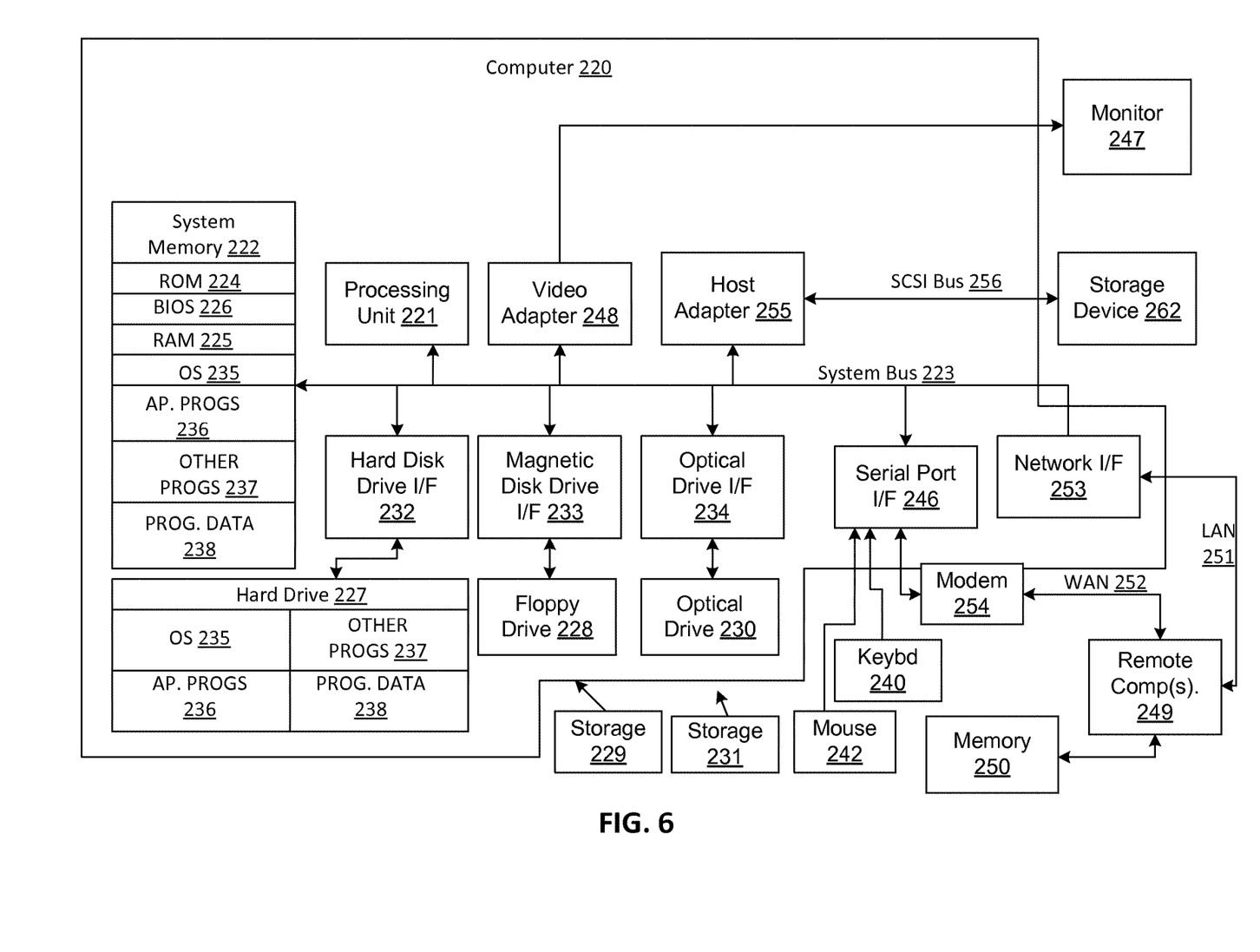
FIG. 6 is an exemplary block diagram representing a general purpose computer system in which aspects of the methods and systems disclosed herein or portions thereof may be incorporated.

FIG. 6 and the following discussion are intended to provide a brief general description of a suitable computing environment in which the methods and systems disclosed herein and/or portions thereof may be implemented. Although not required, the methods and systems disclosed herein may be described in the general context of computer-executable instructions, such as program modules, being executed by a computer, such as a client workstation, server or personal computer. Generally, program modules include routines, programs, objects, components, data structures and the like that perform particular tasks or implement particular abstract data types. Moreover, it should be appreciated the methods and systems disclosed herein and/or portions thereof may be practiced with other computer system configurations, including hand-held devices, multi-processor systems, microprocessor-based or programmable consumer electronics, network PCs, minicomputers, mainframe computers and the like. A processor may be implemented on a single-chip, multiple chips or multiple electrical components with different architectures. The methods and systems disclosed herein may also be practiced in distributed computing environments where tasks are performed by remote processing devices that are linked through a communications network. In a distributed computing environment, program modules may be located in both local and remote memory storage devices.

FIG. 6 is a block diagram representing a general purpose computer system in which aspects of the methods and systems disclosed herein and/or portions thereof may be incorporated. As shown, the exemplary general purpose computing system includes a computer 220 or the like, including a processing unit 221, a system memory 222, and a system bus 223 that couples various system components including the system memory to the processing unit 221. The system bus 223 may be any of several types of bus structures including a memory bus or memory controller, a peripheral bus, and a local bus using any of a variety of bus architectures. The system memory includes read-only memory (ROM) 224 and random access memory (RAM) 225. A basic input/output system 226 (BIOS), containing the basic routines that help to transfer information between elements within the computer 220, such as during start-up, is stored in ROM 224.

The computer 220 may further include a hard disk drive 227 for reading from and writing to a hard disk (not shown), a magnetic disk drive 228 for reading from or writing to a removable magnetic disk 229, and an optical disk drive 230 for reading from or writing to a removable optical disk 231 such as a CD-ROM or other optical media. The hard disk drive 227, magnetic disk drive 228, and optical disk drive 230 are connected to the system bus 223 by a hard disk drive interface 232, a magnetic disk drive interface 233, and an optical drive interface 234, respectively. The drives and their associated computer-readable media provide non-volatile storage of computer readable instructions, data structures, program modules and other data for the computer 220. As described herein, computer-readable media is a tangible article of manufacture and thus not a signal per se.

Although the exemplary environment described herein employs a hard disk, a removable magnetic disk 229, and a removable optical disk 231, it should be appreciated that other types of computer readable media which can store data that is accessible by a computer may also be used in the exemplary operating environment. Such other types of media include, but are not limited to, a magnetic cassette, a flash memory card, a digital video or versatile disk, a Bernoulli cartridge, a random access memory (RAM), a read-only memory (ROM), and the like.

A number of program modules may be stored on the hard disk, magnetic disk 229, optical disk 231, ROM 224 or RAM 225, including an operating system 235, one or more application programs 236, other program modules 237 and program data 238. A user may enter commands and information into the computer 220 through input devices such as a keyboard 240 and pointing device 242. Other input devices (not shown) may include a microphone, joystick, game pad, satellite disk, scanner, or the like. These and other input devices are often connected to the processing unit 221 through a serial port interface 246 that is coupled to the system bus, but may be connected by other interfaces, such as a parallel port, game port, universal serial bus (USB), a wireless interface such as Bluetooth, or the like. A monitor 247 or other type of display device is also connected to the system bus 223 via an interface, such as a video adapter 248. In addition to the monitor 247, a computer may include other peripheral output devices (not shown), such as speakers and printers. The exemplary system of FIG. 6 also includes a host adapter 255, a Small Computer System Interface (SCSI) bus 256, and an external storage device 262 connected to the SCSI bus 256.

The computer 220 may operate in a networked environment using logical connections to one or more remote computers, such as a remote computer 249. The remote computer 249 may be a personal computer, a server, a router, a network PC, a peer device or other common network node, and may include many or all of the elements described above relative to the computer 220, although only a memory storage device 250 has been illustrated in FIG. 6. The logical connections depicted in FIG. 6 include a local area network (LAN) 251 and a wide area network (WAN) 252. Such networking environments are commonplace in offices, enterprise-wide computer networks, intranets, and the Internet.

When used in a LAN networking environment, the computer 220 is connected to the LAN 251 through a network interface or adapter 253. When used in a WAN networking environment, the computer 220 may include a modem 254 or other means for establishing communications over the wide area network 252, such as the Internet. The modem 254, which may be internal or external, is connected to the system bus 223 via the serial port interface 246. In a networked environment, program modules depicted relative to the computer 220, or portions thereof, may be stored in the remote memory storage device. It will be appreciated that the network connections shown are exemplary and other means of establishing a communications link between the computers may be used. Connections discussed herein may be wireless or wireline.

Computer 220 may include a variety of computer readable storage media. Computer readable storage media can be any available media that can be accessed by computer 220 and includes both volatile and nonvolatile media, removable and non-removable media. By way of example, and not limitation, computer readable media may comprise computer storage media and communication media. Computer storage media include both volatile and nonvolatile, removable and non-removable media implemented in any method or technology for storage of information such as computer readable instructions, data structures, program modules or other data. Computer storage media include, but are not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computer 220. Combinations of any of the above should also be included within the scope of computer readable media that may be used to store source code for implementing the methods and systems described herein. Any combination of the features or elements disclosed herein may be used in one or more embodiments.

In describing preferred embodiments of the subject matter of the present disclosure, as illustrated in the Figures, specific terminology is employed for the sake of clarity. The claimed subject matter, however, is not intended to be limited to the specific terminology so selected, and it is to be understood that each specific element includes all technical equivalents that operate in a similar manner to accomplish a similar purpose.

Although features and elements are described above in particular combinations, one of ordinary skill in the art will appreciate that each feature or element can be used alone or in any combination with the other features and elements. This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A device comprising:
   a processor adapted to execute computer-readable instructions; and
   a memory communicatively coupled to said processor, said memory having stored therein computer-readable instructions that when executed by the processor, cause the processor to perform operations comprising:
      generating a chemical exchange saturation transfer pulse sequence for application to tissue,
         said pulse sequence being frequency selective for poly(L-glutamic acid) without a fluorescence conjugated compound in the tissue,
         wherein the PLG creates a chemical exchange saturation transfer (CEST) effect when cleaved by enzymes in the tissue; and
      controlling a magnetic imaging scanner to obtain a magnetic resonance image (MRI) of the tissue to monitor protease activity, in vivo, in the tissue using CEST, wherein the protease activity is the CEST effect when cleaved by enzymes in the tissue.

2. The device of claim 1, further operations of the processor comprising:
   quantifying a state of the tissue based on the use of the MM based on CEST contrast.

3. The device of claim 2, further operations of the processor comprising:
   monitoring a drug in a human based on the quantified state of the tissue.

4. The device of claim 2, further operations of the processor comprising:
   determining efficacy of a drug based on the quantified state of the tissue.

5. The device of claim 2, further operations of the processor comprising:
   determining that the tissue is a malignant tumor or a benign tumor based on the quantified state of the tissue.

6. The device of claim 5, further operations of the processor comprising:
   determining aggressiveness of the tumor based on the quantified state of the tissue.

7. The device of claim 5, further operations of the processor comprising:
   determining heterogeneity of the tumor based on the quantified state of the tissue.

8. A method of imaging poly-L-glutamate, the method comprising:
   injecting a polymer comprising poly(L-glutamic acid), PLG, without a fluorescence conjugated compound, into a tissue, wherein the PLG is broken down by a protease in the tissue, wherein the PLG creates a chemical exchange saturation transfer (CEST) effect when cleaved by enzymes in the tissue; and
   obtaining a magnetic resonance image of the tissue to monitor protease activity, in vivo, in the tissue using CEST, wherein the protease activity is the CEST effect when cleaved by enzymes in the tissue.

9. The method of claim 8, further comprising determining whether a benign tumor or malignant tumor is present in the tissue based on the protease activity.

10. The method of claim 8, further comprising:
    determining therapeutic efficacy of a drug based on the monitored protease activity.

11. The method of claim 8, wherein the protease activity comprises a concentration of glutamate in an area of the tissue.

12. The method of claim 8, further comprising:
    determining aggressiveness of a tumor in the tissue based on the monitored protease activity.

13. The method of claim 8, further operations comprising:
    determining heterogeneity of a tumor in the tissue based on the monitored protease activity.

14. The device of claim 1, wherein the protease comprises cathepsin B.

15. The method of claim 8, wherein the protease comprises cathepsin B.

16. The method of claim 8, further comprising detecting an increase in CEST contrast at 3 ppm due to glutamate formed from cleavage of PLG by protease enzymes.

17. The method of claim 8, further comprising using the protease activity as a bio marker for tumor aggressiveness and tumor heterogeneity.

* * * * *

UNITED STATES PATENT AND TRADEMARK OFFICE
CERTIFICATE OF CORRECTION

PATENT NO. : 10,791,989 B2  
APPLICATION NO. : 14/781441  
DATED : October 6, 2020  
INVENTOR(S) : Haris et al.

Page 1 of 1

It is certified that error appears in the above-identified patent and that said Letters Patent is hereby corrected as shown below:

In the Claims

Column 8, Line 4, Claim 2, Replace "MM based" with -- MRI based --

Signed and Sealed this  
Second Day of February, 2021

Drew Hirshfeld  
*Performing the Functions and Duties of the*  
*Under Secretary of Commerce for Intellectual Property and*  
*Director of the United States Patent and Trademark Office*